US00PP11864P2

(12) United States Plant Patent
Cifrian

(10) Patent No.: US PP11,864 P2
(45) Date of Patent: May 8, 2001

(54) FERN PLANT NAMED 'REGINA'

(75) Inventor: Antonio Cifrian, Malaga (ES)

(73) Assignee: Milestone Agriculture, Inc., Apopka, FL (US)

( * ) Notice: Subject to any disclaimer, the term of this patent is extended or adjusted under 35 U.S.C. 154(b) by 0 days.

(21) Appl. No.: 09/326,325

(22) Filed: Jun. 7, 1999

(51) Int. Cl.[7] ..... A01H 5/00

(52) U.S. Cl. ..... Plt./379
(58) Field of Search ..... Plt./379

*Primary Examiner*—Bruce R. Campbell
*Assistant Examiner*—Anne Marie Grünberg
(74) *Attorney, Agent, or Firm*—C. A. Whealy

(57) ABSTRACT

A distinct cultivar of Fern plant named 'Regina', characterized by its upright and outwardly arching plant habit; relatively compact growth habit; rapid growth rate; durable rachis; numerous pinnae per frond that are dark green, glossy and curly; and closely-spaced pinnae.

3 Drawing Sheets

BACKGROUND OF THE INVENTION

The present invention relates to a new and distinct cultivar of Fern plant, botanically known as *Nephrolepis exaltata*, and hereinafter referred to by the cultivar name Regina.

The new cultivar was discovered by the Inventor in Malaga, Spain, as a naturally-occurring somaclonal variant in a population of tissue-cultured plants of an unnamed selection of *Nephrolepis exaltata*.

Since 1988, asexual reproduction by tissue culture of the new cultivar at Malaga, Spain, has shown that the unique features of this new Fern are stable and retained through more than 100 successive generations of asexual reproduction.

SUMMARY OF THE INVENTION

The new Fern has not been observed under all possible environmental conditions. The phenotype may vary somewhat with variations in environment such as temperature, light intensity and fertilizer regime, without, however, any variance in genotype. The following observations, measurements and comparisons describe plants grown in Apopka, Fla., under conditions generally used in commercial practice.

The following traits have been repeatedly observed and are determined to be the unique characteristics of Regina. These characteristics in combination distinguish Regina as a new and distinct cultivar:

1. Upright and outwardly arching plant habit; symmetrical, rounded and uniform; plants roughly spherical.
2. Relatively compact growth habit.
3. Rapid growth rate.
4. Appropriate for smaller containers and hanging baskets.
5. Durable rachis; plants resist breakage during shipping.
6. Numerous pinnae per frond that are dark green, glossy, curly with finely crenate margins.
7. Closely-spaced pinnae; densely foliated.

The new fern is most similar to its parent cultivar, the unnamed selection of *Nephrolepis exaltata*. However in side-by-side comparisons conducted in Apopka, Fla., the new Fern differs from the unnamed selection of *Nephrolepis exaltata* in the following characteristics:

1. Plants of the new Fern are more compact, more symmetrical and uniform in plant habit than plants of the unnamed selection of *Nephrolepis exaltata*.
2. Rachis are shorter, stronger and more durable on plants of the new Fern compared to plants of the unnamed selection of *Nephrolepis exaltata*.
3. Pinnae are smaller, darker green and curlier on plants of the new Fern compared to plants of the unnamed selection of *Nephrolepis exaltata*.
4. Pinnae are more numerous and more closely-spaced on plants of the new Fern than on plants of the unnamed selection of *Nephrolepis exaltata* which give a more densely foliated appearance to the new Fern.

BREIF DESCRIPTION OF THE PHOTOGRAPHS

The accompanying colored photographs illustrate the overall appearance of the new cultivar, showing the colors as true as it is reasonably possible to attain in colored reproductions of this type.

Colors in the photographs may differ slightly from the color values sighted in the detailed botanical description which more accurately describe the actual colors of the new Fern. The photograph on the first sheet comprises a side perspective view of a typical hanging basket plant of 'Regina'.

The photograph on the second sheet comprises a side perspective view of a typical hanging basket of 'Regina' (top) compared to a comparable hanging basket of the unnamed selection of *Nephrolepis exaltata* (bottom).

The photograph on the third sheet comprises a close-up view of typical fronds of the unnamed selection of *Nephrolepis exaltata* (left) and 'Regina' (right). Pinnae and rachis colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. Measurements and numerical values represent averages for typical five-month old plants grown in Apopka, Fla., in 20-cm hanging basket containers under a polypropylenecovered shade house that provided a 75 percent light reduction with day temperatures of about 15 to 27° C and night temperatures of about 10 to 15° C.

Botanical classification: *Nephrolepis exaltata* cultivar Regina.

Parentage: Naturally-occurring somaclonal variant of an unnamed selection of *Nephrolepis exaltata*, not patented.

Propagation: By tissue culture; stolon and rhizome development has not been observed.

Rooting time:

*Time to initiate roots.*—About 7 to 10 days.

*Time to develop roots.*—About 28 to 42 days.

Plant description:

*Plant shape.*—Roughly spherical; rounded and uniform.

*Growth habit.*—Upright and outwardly arching; symmetrical; relatively compact; appropriate for smaller pots, 10 to 15-cm, and up to 20-cm hanging baskets.

*Plant height.*—About 43 cm from soil line to top of the plant plane.

*Plant width.*—About 81 cm.

*Overall plant vigor.*—Moderate.

*Growth rate.*—Rapid.

*Crop time.*—About 5 months are required to produce a finished 20-cm hanging baskets.

*Frond description.*—Leaf arrangement: One-pinnate. Front length: About 39 cm. Frond width: About 6.8 cm. Rachis diameter: About 1 mm. Rachis color: Brown, close to 166A.

*Pinnae description.*—Shape: Linear. Length: About 3.5 cm. Width: About 1.1 cm. Quantity of pinnae: Numerous, about 102 per frond. Margin: Finely crenate. Apex: Acute. Base: Truncate, asymmetrical. Aspect: Undulate along axis. Attachment: Sessile. Texture: Glabrous and glossy. Color: Immature, upper surface: Darker than 146A to 147A. Immature, lower surface: Darker than 146A to 147A. Mature, upper surface: Close to 147A. Mature, lower surface: 147A. Venation pattern: Pinnate.

*Spores.*—None observed.

Disease resistance: Resistance to diseases common to *Nephrolepis exaltata* has not been observed.

It is claimed:

1. A new and distinct cultivar of Fern plant named 'Regina', as illustrated and described.

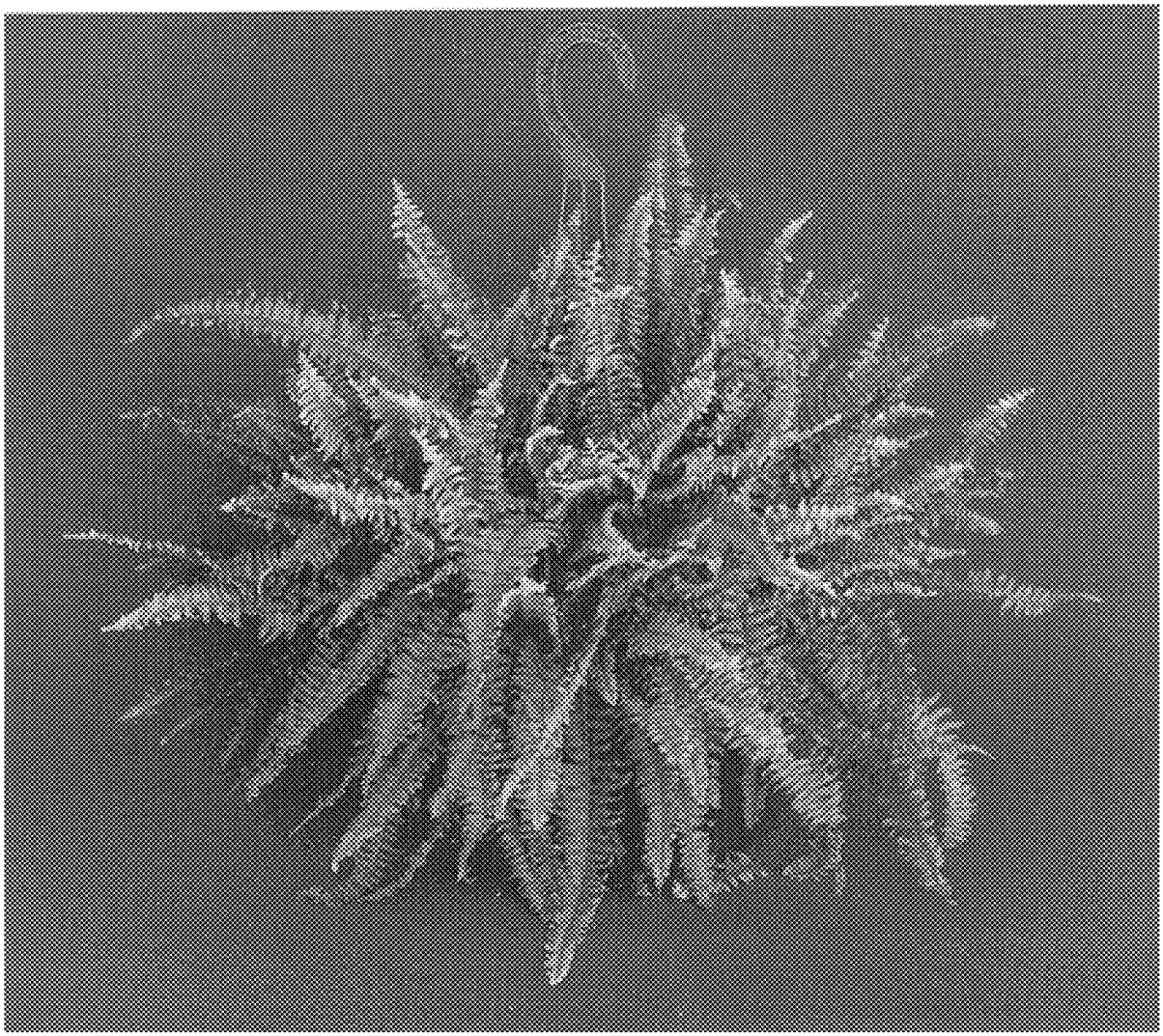

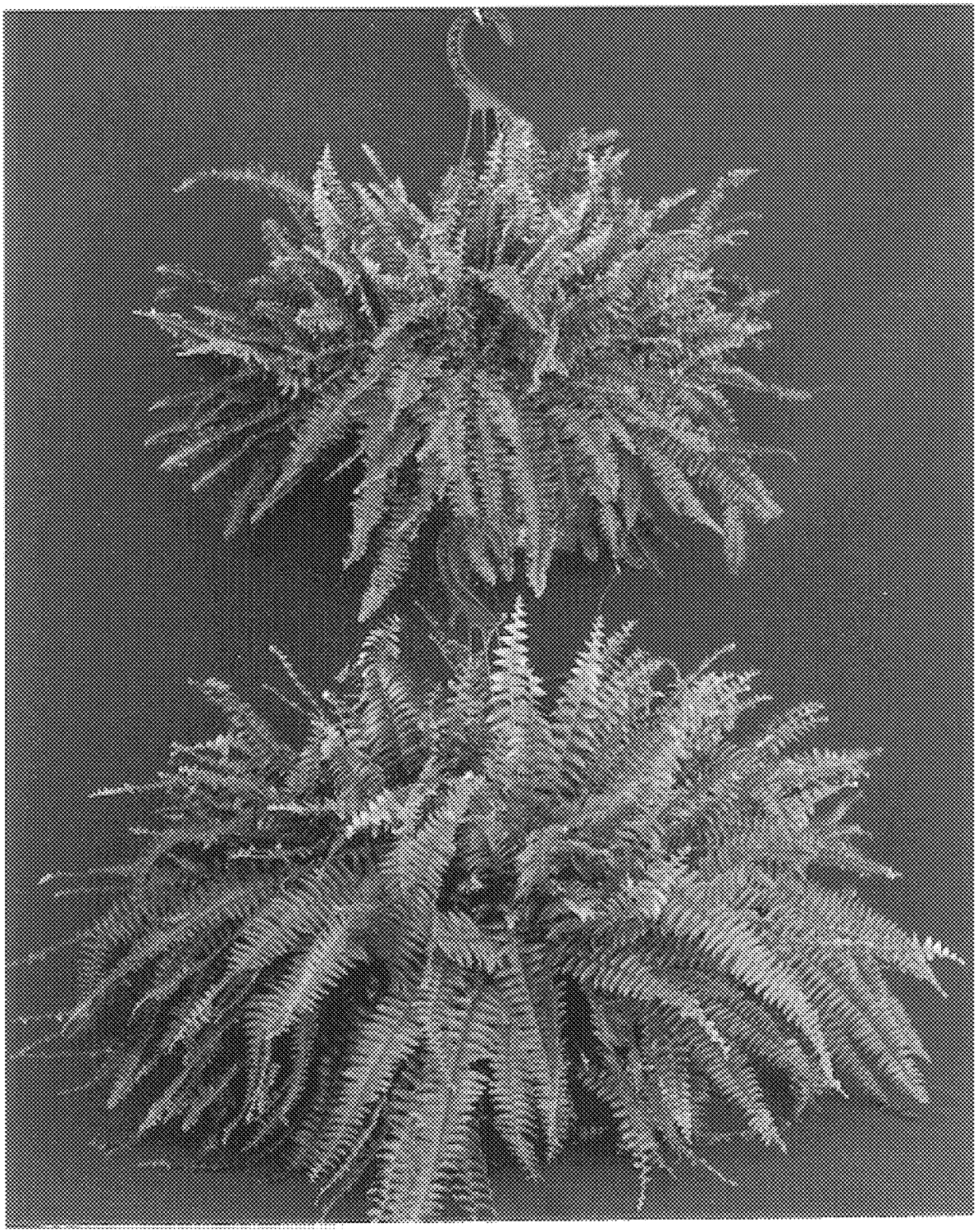

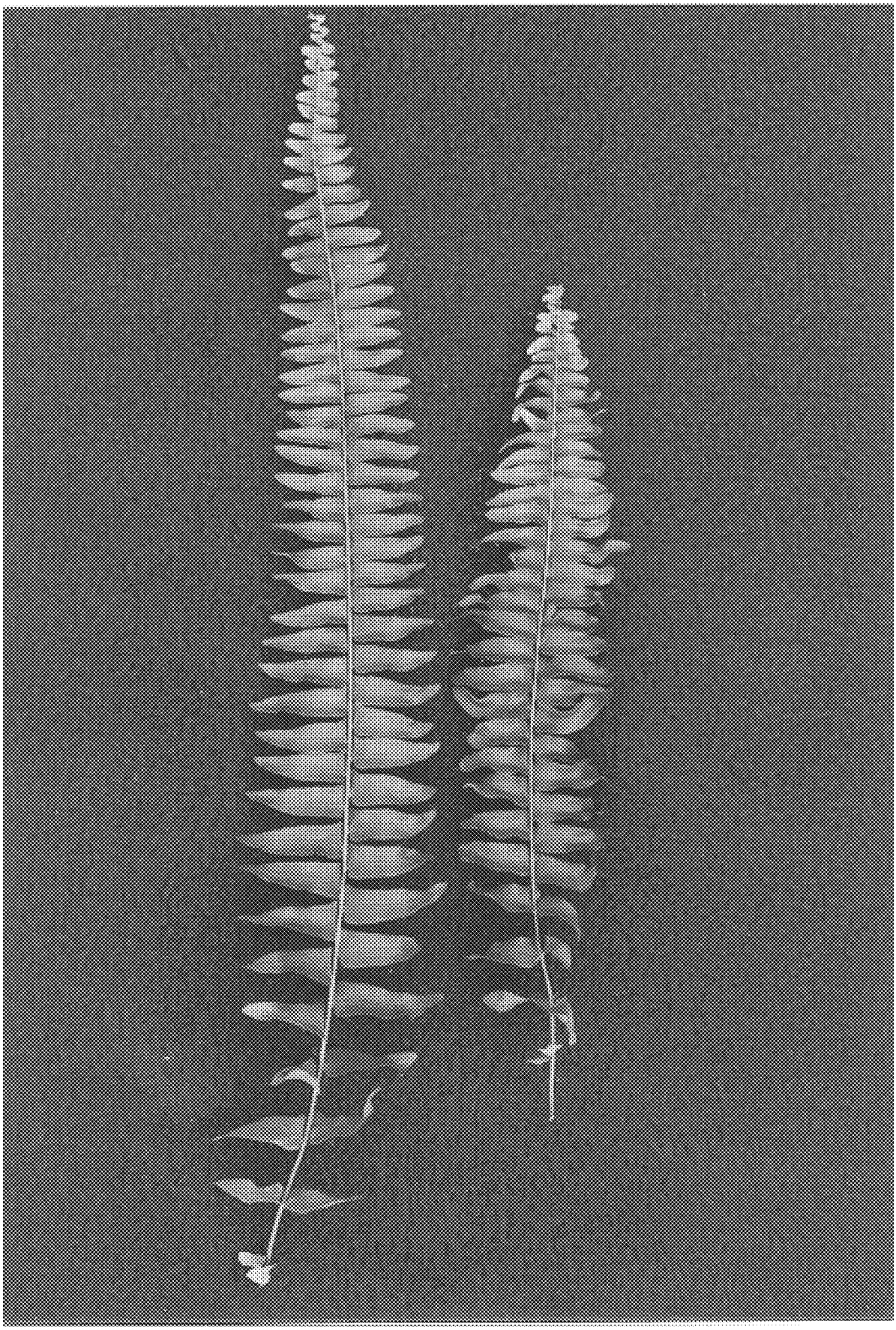

* * * * *